United States Patent
Masuko

[11] Patent Number: 5,981,202
[45] Date of Patent: *Nov. 9, 1999

[54] TWO-DIMENSIONAL SOLID PHASE ASSAY

[75] Inventor: Masayuki Masuko, Hamamatsu, Japan

[73] Assignee: Biosensor Laboratories Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/397,973

[22] Filed: Mar. 3, 1995

[30]  Foreign Application Priority Data

Nov. 15, 1994 [JP] Japan .................................. 6-280377

[51] Int. Cl.$^6$ .......................... G01N 33/53; G01N 33/551
[52] U.S. Cl. .......................... 435/7.9; 435/7.92; 435/7.94; 435/21; 435/25; 435/28; 435/962; 435/968; 435/970; 435/973; 435/6; 436/524; 436/535; 436/809
[58] Field of Search .................................. 435/7.9, 7.92, 435/7.94, 21, 25, 28, 962, 968, 970, 973; 436/524–535, 809, 6

[56]  References Cited

U.S. PATENT DOCUMENTS

| | | |
|---|---|---|
| 3,690,837 | 9/1972 | Witz et al. . |
| 4,652,533 | 3/1987 | Jolley ........................................ 436/518 |
| 4,948,975 | 8/1990 | Erwin et al. .......................... 250/361 C |
| 5,089,424 | 2/1992 | Khalil et al. ............................. 436/518 |
| 5,096,807 | 3/1992 | Leaback ........................................ 435/6 |
| 5,106,732 | 4/1992 | Kondo et al. .............................. 435/28 |
| 5,108,704 | 4/1992 | Bowers et al. ............................. 422/70 |
| 5,133,866 | 7/1992 | Kauvar ..................................... 210/635 |
| 5,275,951 | 1/1994 | Chow et al. ............................... 436/50 |
| 5,320,944 | 6/1994 | Okada et al. .......................... 435/7.94 |
| 5,415,839 | 5/1995 | Zaun et al. ................................. 422/64 |
| 5,508,200 | 4/1996 | Tiffany et al. ............................. 436/44 |
| 5,512,451 | 4/1996 | Kricka ....................................... 435/28 |

FOREIGN PATENT DOCUMENTS

| | | |
|---|---|---|
| 0194132A2 | 9/1986 | European Pat. Off. . |
| 0421736A2 | 4/1991 | European Pat. Off. . |
| 251063 | 2/1990 | Japan . |
| 2207245A | 1/1989 | United Kingdom . |

OTHER PUBLICATIONS

Akhavan–Tafti et al., "CCD Camera Imaging for the Chemiluminescent Detecting of Enzymes Using New Ultrasensitive Reagents," J. Biolumin. Chemilumin 9(3): 155–164, 1994.

Hooper et al., "Low–Light Imaging Technology in the Life Sciences," J. Biolumin. Chemilumin. 9(3): 113–122, 1994.

(List continued on next page.)

*Primary Examiner*—Christopher L. Chin
*Assistant Examiner*—Pensee T. Do
*Attorney, Agent, or Firm*—Cushman Darby & Cushman

[57]  ABSTRACT

A method for assaying a substance is provided in which an optical image is obtained from spots of light emitted from a chemiluminescent material capable of undergoing a luminescent reaction. The method comprises: (a) a step of distributing solid particles on the surface of a support, the solid particles having a diameter of not more than 100 $\mu$m and on its surface carrying an antibody being able to catch a catalyst previously bound to the second antibody (or its analogue, such as Fab') through binding an antigen, and the support being permeable to a liquid and capable of absorbing light emitted from chemiluminescent material; (b) a step of immersing the support into a solution containing the chemiluminescent material to bring the catalyst over the support into contact with the chemiluminescent material to cause luminescent reactions including fluorescence; (c) a step of two-dimensionally picking up an optical image including an image formed by luminescence and fluorescence, and converting it into electric signals; (d) a step of storing the measured two-dimensional image data of the optical image in a image processing device; and (e) a step of manipulating the stored signals to form a new image in the same processing device.

7 Claims, 4 Drawing Sheets

OTHER PUBLICATIONS

Patent Abstracts of Japan, Publication No. 020.51063 Publication Date: Feb. 21, 1990 "Detection of Specific Antigen Or Fine Object Having The Same.".

Maly et al, "A Single–Photon Imaging System for the Simultaneous Quantitation of Luminescent Emissions from Multiple Samples", Analytical Biochemistry, vol. 168, 1988, pp. 462–469.

Motsenbocker et al, "Improvements to Enhanced Horseradish Peroxidase Detection Sensitivity", J. Biolumin Chemilumin 1994, vol. 9, pp. 15–20.

Ugelstad et al, "Magnetic Polymer Particles fo Cell Separation", Antibody–Mediated Methods, pp. 74–77 Bone Marrow Transplantation, V2, S2, 1987.

Ishikawa et al, "Enzyme–Labeling of Antibodiew and Their Fragments for Enzyme Immunoassay and Immunohistochemical Staining", Journal of Immunoassay, 4(3), 1983, pp. 209–327.

Fig. 3A    Fig. 3B
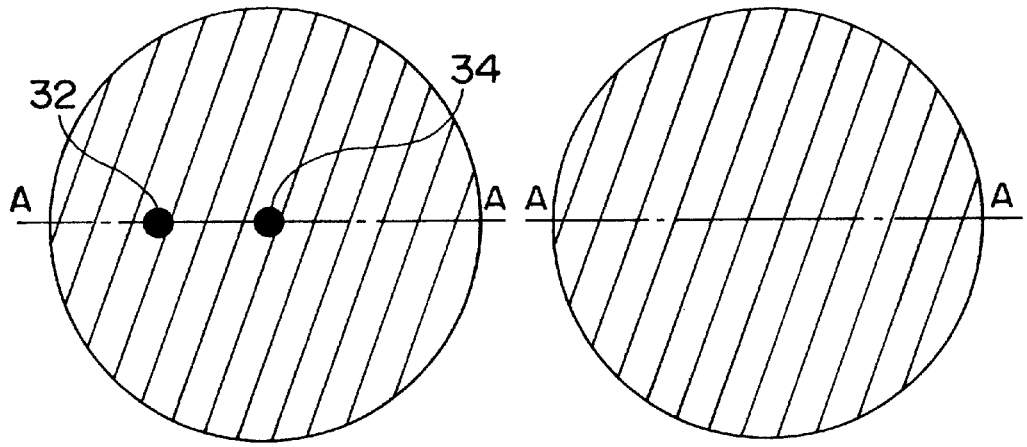
Fig. 3C    Fig. 3D
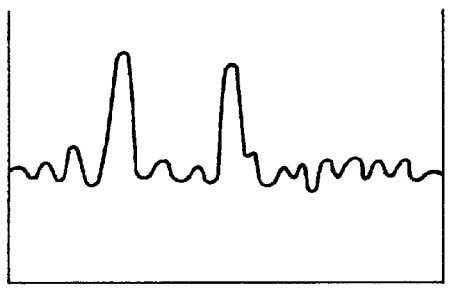 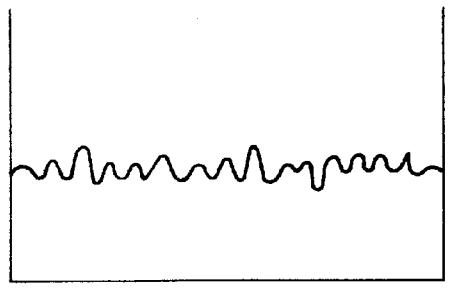
Fig. 3E
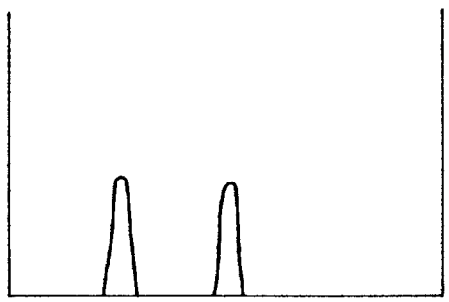

TWO-DIMENSIONAL SOLID PHASE ASSAY

BACKGROUND OF THE INVENTION

1. Field of the Invention

The present invention relates to methods for determination of a substance by measurement of light emitted from a specimen prepared based on an antigen-antibody reaction. In particular, the present invention relates to solid phase immunoassays by use of fine particulate materials.

2. Related Background Art

The antigen-antibody reaction is one of the reactions with a high affinity and high specificity. The immunoassay method using the antigen-antibody reaction allows to detect objects such as living tissues, cells, and bacteria, with high sensitivity. Further, the immunoassay method is simple in operation and applicable to various objects. Therefore, this method is widely used for measurements in biology and biochemistry. In recent years, various methods are being actively developed featuring such advantages, especially for ultrasensitive assays of trace substances; for example, interleukin 6 in human blood.

In conventional fine-particle solid phase immunoassay by light measurements, a point sensor is generally used to determine the intensity of signals from the sample. In enzyme immunoassays, for example, an enzyme activity is either transduced into fluorescent light or other emissions. And then the light can be detected by a fluorescence spectrophotomer and other instruments including a photomultiplier tube as a detector.

In point sensing with a point sensor, however, the measurement is affected by background noises emitted from the entire area of the sample's optical image. The noises typically come from contaminants in the sample. When the signal is weak in the point sensing, the sum of those noises across the image is much higher than the sum of the intensity of the signal from the object, providing a low S/N ratio. This makes high sensitivity measurement infeasible.

Maly, F. E., et al. (Anal. Biochem., 168 462–469(1988)) provides an immunoassay method in which a microtiter plate is used as the solid phase for objects, and the light emitted from each of the wells of the microtiter plate is detected by a two-dimensional detector. This method enables simultaneous detection of signals emitted from the individual wells. The method of Maly, however, is equivalent to a method of simultaneous point sensing for each of the wells. Maly discusses no countermeasure against the high background noise over the signals from the light-emitting reagent in the respective microtiter plate wells. Japanese Patent Application S63-201561 describes an immunoassay method that enable to obtain a two-dimensional optical image of fine particles and to counts the number of the particles. This method, however, is intended to determine the number of particles by binarizing the intensity of light signals from the fine particles, but is not directed to determine the total light intensity of an object with sufficiently high sensitivity with an improved S/N ratio.

SUMMARY OF THE INVENTION

The present invention is intended to provide an assay for a trace substance with less noise and an improved S/N ratio. The assay method of the present invention comprises the following steps:

(a) distributing solid particles two-dimensionally and substantially uniformly on the surface of a support; said solid particles having a diameter of not more than 100 $\mu$m and carrying on the surface thereof an immunological complex; the immunological complex comprising (i) a target antigen, (ii) a catalyst for luminescent reaction of a chemiluminescent material, (iii) a first antibody for the target antigen being bound to the surface of the particles, (iv) a second antibody for the target antigen being bound to the catalyst, wherein the target antigen binds to both the first antibody and the second antibody, and wherein the catalyst being conjugated to the second antibody; the support being permeable to a liquid and capable of absorbing light emitted from the chemiluminescent material;

(b) immersing the catalyst over the particles on the support into a reaction mixture for light emission;

(c) extracting two-dimensional image data from optical images, including an image formed by light of the chemiluminescent reaction, with an image pick-up device which two-dimensionally picks up an optical image formed by the incident light and converts the incident light intensity for respective light-receiving sites (or picture elements) into electric signals;

(d) collecting and storing the acquired two-dimensional image data of the optical image (original image data) in a digital device; and (e) assaying the substance based on the measured two-dimensional image data collected by the processing device.

The catalyst may be an enzyme in the assay method of the present invention. The chemiluminescent material may be a substrate for the enzyme in the assay method of the present invention.

The assay method of the present invention may further comprise the following steps:

penetrating the chemiluminescent material into a support having no fine particle thereon;

picking up a background optical image of the support having no fine particle with the image pick-up device;

converting the incident light intensity for respective light-receiving sites (or picture elements) into electric signals to obtain the data of the two-dimensional background image;

collecting and storing the acquired two-dimensional background image data in the digital device prior to the steps of assaying the substance; and subtracting the background image data from the original image data in the assaying steps.

The assay method of the present invention may use an image pick-up device which further comprises an image-intensifying optical device for intensifying the incident light intensity of the optical image and outputting the intensified optical image and converting the image into electric signals.

The present invention will be fully understood from the detailed description given herein below and the accompanying drawings which are given by means of illustration only. However, the description may not limit the right of the present invention.

Further scope of applicability of the present invention will become apparent from the detailed description given hereinafter. However, it should be noted that the detailed description and specific examples, although indicating preferred embodiments of the invention, are given by means of illustration only. Various changes and modifications within the spirit and scope of the invention will become apparent to those skilled in the art from this detailed description.

BRIEF DESCRIPTION OF THE DRAWINGS

FIGS. 3A to 3E show image processing steps in an embodiment of the present invention: FIG. 3A and FIG. 3B are plane views of the inside of the Petri dishes; FIG. 3C and FIG. 3D are graphs showing intensity distribution of the picked-up image in the direction of the diameter of the Petri dish; FIG. 3E are graphs showing intensity distribution of the processed image.

DETAILED DESCRIPTION OF THE INVENTION

In the present invention, a luminescent object is distributed or scattered two-dimensionally and uniformly onto a support, and immersed in a solution containing a chemiluminescent material on the support. Then, an optical image which includes light from the target object can be picked up and the intensities of respective picture elements in the optical image are collected and converted into the electrical signals. Then the electrical signals are stored as the two-dimensional image data. The background image are also picked up, and the background image data are stored, in the same manner described above.

Thereby the optical image, which is generally a mixture of the undesirable background noises and the required signals from the target object, can be processed for each picture element. Therefore, noises can be definitely cut off and only the required signals can be acquired.

The assay method of the present invention employs a support which is permeable to a liquid and capable of absorbing light, whereby the catalyst which serves as the marker of the target object can readily contact a solution containing a chemiluminescent material and the light coming from the portions other than the target object is absorbed without troublesome treatment in the measurement.

Preferred Embodiment

Figure 1:
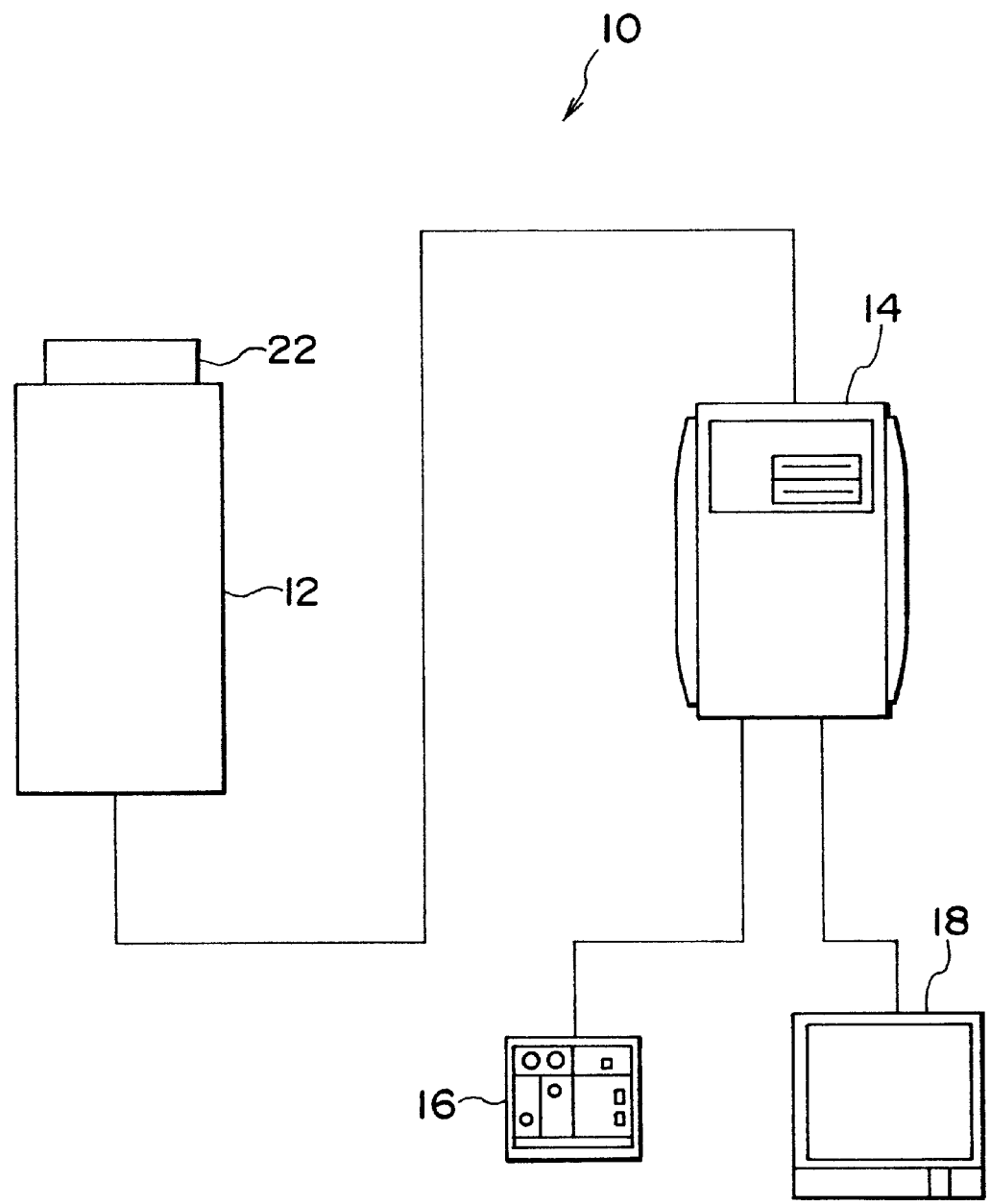
FIG. 1 illustrates the constitution of the assaying apparatus employed in an embodiment of the present invention.

FIG. 1 shows an observation apparatus 10 suitable for the assay method of the present invention. The observation apparatus 10 consists of the following components: a camera 12 as an image pick-up device for picking up an optical image, transducing it into electric signals, and outputting it; an image processor 14 which stores the output signals from the camera 12 and processes the signals in a predetermined manner; a controller 16 which controls the camera 12; and a CRT monitor 18 which displays the image based on the image data stored or processed by the image processor 14. Onto the light entrance window of the camera 12, a chamber 22 is provided for containing the target object. The camera picks up the image light emitted from the marker bound to the object in the chamber 22.

In the preferred embodiments of the present invention described below, a photon-counting camera C5031 (manufactured by Hamamatsu Photonics K. K.) is used as the camera 12, and an image processing system ARGUS 100 (manufactured by Hamamatsu Photonics K. K.) is used as the device system comprising the image processor 14, the controller 16, and the CRT monitor 18.

The observation apparatus useful for practicing the method according to the present invention is not limited to the above apparatus or system. Any known image processing system may be used without limitation, provided that the apparatus is capable of picking up an optical image by picture element, transducing it into electric signals which correspond to respective picture elements, and processing it as required. For example, the image pick-up device may comprise an image intensifier which transduces photons of the optical image into electrons, multiplies the electrons, and finally re-convert those electrons into an amplified optical image. The image pick-up device may also be a cooled CCD camera.

The chamber 22 may typically be a Petri dish. The bottom of the Petri dish may be formed of an optical waveguide such as an optical fiber plate. In this case, preferably, an image intensifier is connected with the entrance of the camera, and the Petri dish is placed onto the entrance window of the image intensifier such that the waveguide of the entrance window of the image intensifier is optically connected to the waveguide of the bottom of the Petri dish.

Otherwise, a magnification device such as a macro-lens or a microscope may be attached to the camera, and the chamber 22 may be placed under the camera 12 differently from the illustration of FIG. 1 to pick up the optical image from the upside of the chamber 22.

In this embodiment, a trace amount of porcine insulin as the target object was detected via a solid phase enzyme immunoassay method.

Figure 2:
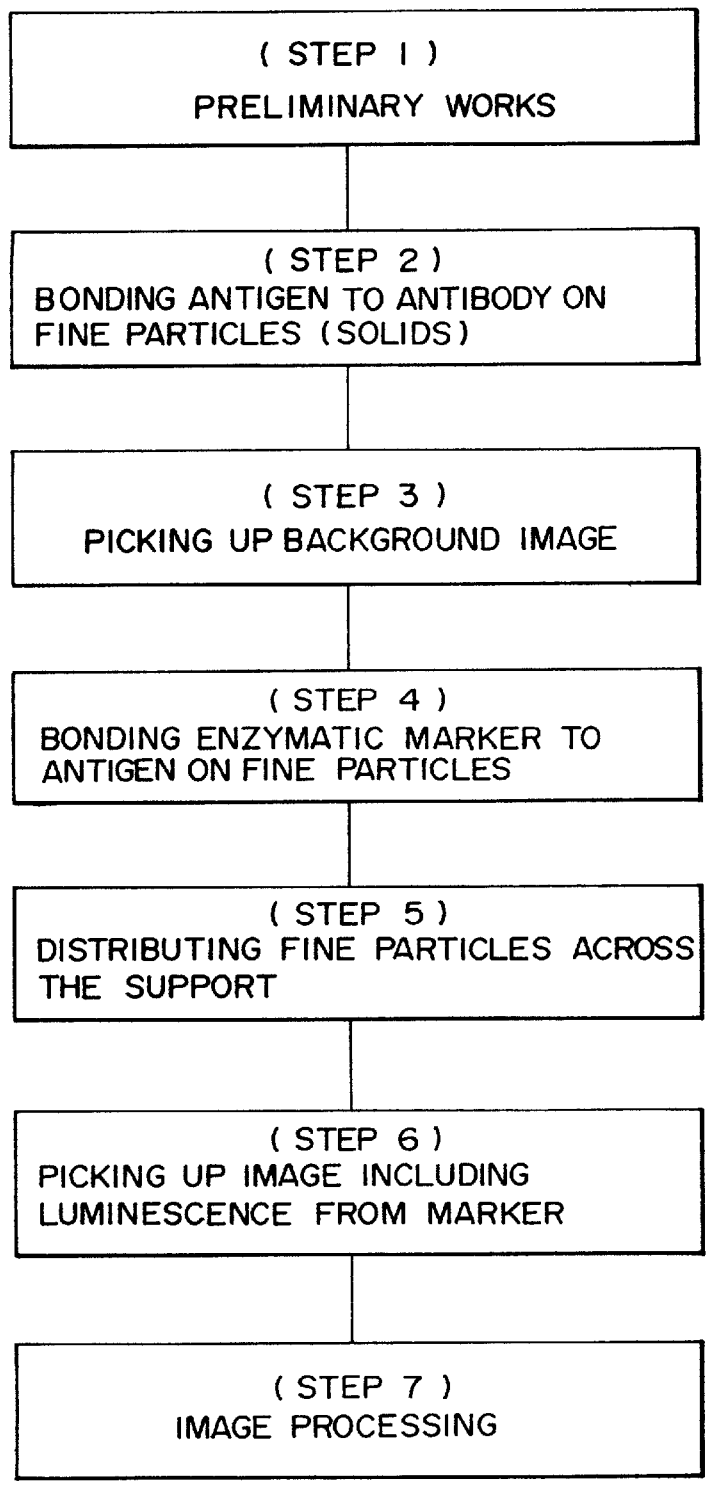
FIG. 2 is a flow chart showing the steps in an embodiment of the present invention.

FIG. 2 is a flow chart showing the steps of the analysis in the present embodiment. The steps were described below in detail. An antibody which is specific to porcine insulin (target antigen) as a detection target, was adsorbed onto fine particles. Then porcine insulin (antigen) was bound to the first antibody over fine particles. An enzyme that promotes a luminescent reaction or fluorescent reaction was bound to the antigen through an adequate carrier such as the second antibody to porcine insulin. In other word, the enzyme is conjugated with the second antibody, so that the conjugated enzyme of marker can bind to the target antigen via antigen-antibody reaction. Finally the solid phase (fine particles) having the target object and its marker enzyme was obtained to transduce the quantity of the target object into light signals through a catalytic reaction of the marker. These fine particles was dispersed or scattered two-dimensionally onto a support surface capable of absorbing visible light (namely, a black support). A solution which contains luminol, a chemiluminescent material, was allowed to penetrate into the support to induce chemiluminescence. The optical image of the support was picked up and then processed, using the system shown in FIG. 1.

This embodiment is described in more detail below.

(1) Preliminary Works ("Step 1" in FIG. 2)

(Preparation of Dilution Solution Containing The Target Object)

Block Ace Solution (produced by Snow Brand Milk Products Co., Ltd.) was diluted four-fold with 0.1M phosphate buffer solution (pH 7) (hereinafter referred to as "dilution solution"). Therein, porcine insulin (produced by Wako Pure Chemical Industries, Ltd.) to be detected was dissolved to form the original solution of the object. The light absorbance of this original solution was measured and therefrom the precise concentration was calculated by reference to the known molar extinction coefficient. A series of diluted solutions containing different concentrations of the porcine insulin were prepared by adding different aliquot of the original solution to the dilution solutions. The porcine insulin concentrations of the respective solutions were calculated from the above precise concentration of the original solution and the dilution ratio.

(Purification of Antibody)

The anti-porcine insulin antibody, namely the antibody which can specifically bind to the antigenic porcine insulin, was separated and purified from anti-porcine insulin antiserum. Firstly, the anti-porcine insulin antiserum was fractionated on a Protein A Sepharose column (produced by Amersham Co.). The active fractions were combined and further purified by affinity chromatography on a insulin Sepharose or insulin agarose (produced by Sigma Co.) column.

(Adsorption of Antigen Onto Fine Particles)

The fine particulate material as the solid phase was commercially available as magnetic beads, "DYNABEADS, M-280 Tosyl-activated" (manufactured by Nippon Dynal Co., Ltd.). The fine particles had a particle diameter of approximately 28 μm. The above purified anti-porcine insulin antibody was adsorbed onto the surface of the magnetic fine particles in a liquid suspension state according to the operation manual provided by the manufacturer. The suspension of the magnetic particulate material having the anti-porcine insulin antibody thus prepared was stored according to the above operation manual.

(Preparation of Enzyme for Promoting Luminescent Reaction)

Luminol was used as the chemiluminescent material. A peroxidase was used as the marker enzyme for promoting the luminescent reaction of luminol. In this embodiment, the marker enzyme (horseradish peroxidase) was specifically conjugated to Fab' derived from anti-porcine insulin antibody (hereinafter referred to as "Fab'-HRP conjugate"). In other words, horseradish peroxidase conjugated with the Fab' was used as the conjugated enzyme of marker. The Fab'-HRP conjugate was prepared by the maleimide method described by Ishikawa, E., et al. (J. Immunoassay, vol. 4, pp. 209–327 (1983)), the disclosure of which is hereby incorporated by reference. The obtained Fab'-HRP conjugate was further purified by chromatography on a Sephacryl S-400 (produced by Pharmacia Co) column.

The marker enzyme available for the present invention is not limited to the horseradish peroxidase, but any known enzyme may be employed which will induce luminescence from a chemiluminescent material. Further, a catalyst like porphyrin which promotes chemiluminescent reaction of luminol may be employed as the marker in place of the enzyme. The chemiluminescent matter is not limited to luminol, but any other known chemiluminescent materials may be used, such as indole derivatives and acridine derivatives.

(Preparation of Reaction Solution Containing Chemiluminescent Matter)

The composition and the formulation of the solution of luminol as the chemiluminescent material employed in this embodiment was the same as described by Motsenbocker, M. A.; and Kondo, K (J. Biolum., Vol. 9, pp. 15–20 (1944)), which is hereby incorporated by reference. Specifically, 1 ml of the reaction solution employed in this embodiment contained 4.0 mM of luminol, 50 μM of p-phenylphenol, 0.1 mM of EDTA, and 100 mM of tris-hydrochloric acid buffer solution (pH 8.5). In this embodiment, the luminol for the reaction solution was highly purified via recrystallization because the purity of the luminol seriously affects the intensity of the chemiluminescence. The solution was prepared just before the practice of the assay.

(2) Antigen-Antibody Reaction

The operations described below are typical ELISAs (enzyme-linked immunosorbent assays) using fine particles as the solid phase.

(Bonding or Binding of Antigen to Antibody on Fine Particles: "Step 2" in FIG. 2)

A suitable amount of the liquid suspension containing the magnetic fine particles having the aforementioned anti-porcine insulin antibody was placed in a test tube. The suspension was separated into the liquid portion and the solid portion(particles), by the operation that the magnetic particles were being attracted magnetically, and the liquid portion of the suspension was discarded. Then 0.1 ml of the above prepared diluted solution containing the porcine insulin was added. The test tube was shaken vigorously at room temperature for one hour. Then the liquid portion was discarded by the same method mentioned above. The fine particles were washed as described below.

A washing solution was prepared by adding Tween-20 as the surfactant to a concentration of 0.02% into the Block AceRM solution diluted with 0.1M phosphate buffer (pH 7.0). 0.2 ml of the washing solution was added to the above test tube holding the fine particles. The test tube was shaken at room temperature for one hour, and the liquid portion was discarded with the magnetic particles attracted magnetically. The above washing operation was carried out three times.

(Bonding or Labeling of Conjugated Enzyme of Marker to Antigen: "Step 4" in FIG. 2)

To the test tube, was added 0.1 ml of a solution of Fab'-HRP diluted with the aforementioned dilution solution (0.1 ml of this solution contained 100 fmol of Fab'-HRP conjugate). The test tube was shaken at room temperature for one hour, and the liquid portion was discarded by the same method described previously. Then the washing with the above washing solution was carried out three times in the same manner as described above.

In such a manner, fine particles for the antigen assay were prepared having a combination of (fine particles)-(antibody)-(antigen)-(conjugated enzyme of marker) linked in this order. The fine particles were stored at 0° C. in a form of suspension with 0.1M phosphate buffer solution (pH 7.0).

(3) Measurement (Distributing and Adsorbing Fine Particles on Support: "Step 5" in FIG. 2)

The fine particles for the antigen assay were dispersed or scattered and adsorbed two-dimensionally on a support capable of absorbing visible light. In this embodiment, the support was a black nitrocellulose membrane filter of 2.5 cm in diameter. However, any known adsorption filter may be used as the support, provided that it is capable of adsorbing the noise in the chemiluminescent reaction and allowing liquid penetration. For example, colored nylon membrane filters, colored PVDF (polyvinylidene difluoride) filters are useful for the assay method according to the present invention. The "color" of the filter is preferably black.

A black nitrocellulose membrane filter (manufactured by Toyo Roshi K. K.) was set in Dot-Blot Apparatus (manufactured by Millipore Co.). Thereto, 10 μl of the above liquid suspension containing the fine particles was supplied through the holes of the Dot-Blot Apparatus. Thus the fine particles in the liquid suspension were scattered and attached two-dimensionally and uniformly around the center portion of the membrane filter.

(Measurement of Emission of Light from Marker Bonded to Object: "Step 6" in FIG. 2)

A reaction solution containing luminol therein was soaked into the black nitrocellulose membrane filter carrying thereon the fine particles over which the object is bonded. Thereby the enzyme markers encountered the luminol to induce the chemiluminescent reaction. This reaction was observed using the observation apparatus shown in FIG. 1.

The membrane filter was taken out from the Dot-Blot Apparatus and then placed in a chamber (Petri dish PD-47, manufactured by Toyo Roshi K. K.) holding 1.2 ml of the luminol-containing reaction solution with the particle-carrying side of the filter against the surface of the entrance window of a image pick-up device. At this time, the Fab'-HRP conjugate marking the porcine insulin bound to the antibody on the surface of the fine particles began to catalyze the chemiluminescent reaction in the reaction solution to cause light emission selectively at the portion carrying the porcine insulin.

The two-dimensional optical image formed by the light emitted from the Fab'-HRP in the chamber 22 (Petri dish) placed in the light entrance window of the photon-counting camera 12 was obtained two-dimensionally for one minute.

(3) Image Processing: "Steps 3 and 7 in FIG. 2)

FIGS. 3A to 3E illustrate the image processing procedure in this embodiment. FIG. 3A and FIG. 3B are plan views of the picked-up image portion of the Petri dish. FIG. 3C, FIG. 3D, and FIG. 3E are graphs showing intensity distribution of the light image in the diameter direction, the ordinates showing the intensity, and the abscissas showing the positions in the diameter direction. FIG. 3C shows the luminescence distribution of the portion containing the object 32, 34 emitting light at the section A—A in FIG. 3A, and FIG. 3D shows the portion not containing the object. FIG. 3E shows the image after processing of the picked-up image of this embodiment.

The image was processed as follows. Before the observation of the black nitrocellulose membrane filter containing the fine particles, an optical image of the nitrocellulose membrane filter without the fine particles was picked up by the use of the pick-up apparatus shown in FIG. 1, in the same manner as the above measurement (namely, the measurement of the luminescence given by the labeled marker). This result are shown in FIG. 3B and FIG. 3D. The acquired two-dimensional data (background image) was stored in the image processor. Thereafter, the optical image including the above chemiluminescent image from the marker label (original image) was picked up, and the acquired two-dimensional data (FIG. 3A and FIG. 3C) was stored in the same image processor. The two-dimensional data were stored in such a manner that the numerical values corresponding to the detected luminescence for respective picture elements were arranged in the order of the picture elements.

The acquired image have included many noise components which came from the impurities in the reaction solution, as shown in FIG. 3C. in particular, trace amount of the object with much noise components, such as the image having ordinal luminescence distribution as in FIG. 3C, are not able to be sufficiently assayed by point sensing with luminometers. In the point sensing, all of the noises included in the image are acquired so that the chemiluminescence from trace amount of the objects are buried in the noises.

On the contrary, in the preferred embodiment of the present invention, image processing was conducted to subtract the luminescence signals of the individual picture elements of the background image (FIG. 3D) from those of the corresponding picture elements of the original image. (FIG. 3C). The processed data (FIG. 3E) so obtained was stored in the image processor.

As shown in FIG. 3E, the image processing of subtracting the background image data from the original image data results in effective reduction of the noises, giving the images shown in FIG. 3A and FIG. 3C, so that it enables to easily extract data of luminescence 32, 34 from the original image. The extracted luminescence data have the useful information that indicates not only the existence of the objects but also the quantities of the objects.

Figure 4:
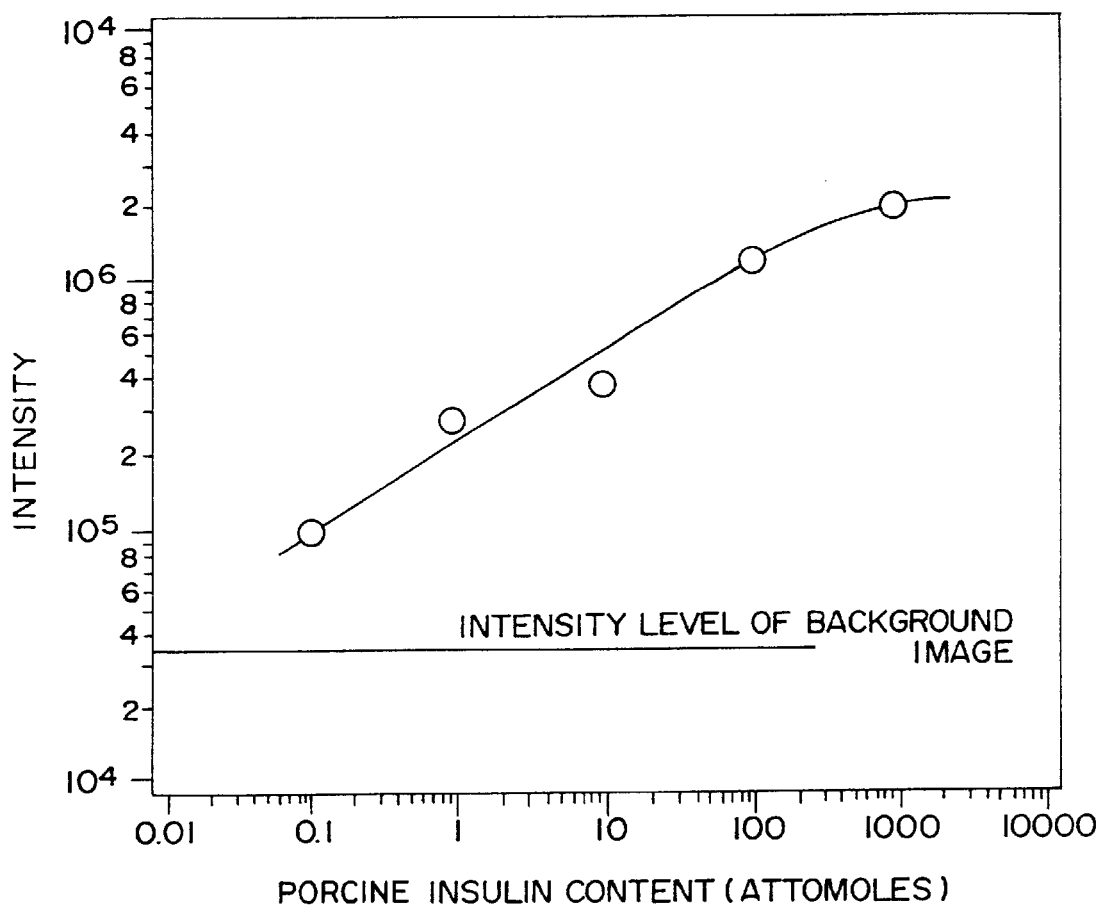
FIG. 4 is a graph showing dependency of the intensity of the luminescence on the content of porcine insulin.

The detection of the porcine insulin was conducted for the series of the diluted solution prepared as described above. FIG. 4 is a graph showing the dependence of the intensity of the emitted light on the amount of the porcine insulin. FIG. 4 also shows the level of the background luminescence intensity.

According to the definition of the detection limit of the insulin as the intensity twice of the background light in consideration of the reproducibility of the measured data, the detection limit of the porcine insulin was 0.1 attomole in this embodiment.

For comparison, the measurement was conducted by a conventional technique employing a luminometer for point sensing with other conditions being the same as in the embodiment of the present invention. In this point sensing, the detection limit was 1 attomole. The porcine insulin less than this detection limit was not detectable.

Accordingly, the two-dimensional solid phase assay of this embodiment of the present invention was shown to lower the detection limit by about one decimal order in comparison with the point sensing. Therefore, the method according to the invention is highly effective for detection of extremely low amount of an object.

The present invention enables measurements with high sensitivity, improving a S/N ratio by cutting two-dimensionally the related noise such that the good optical image is formed by visible light emitted by a catalyst fixed through the antigen-antibody reaction.

The two-dimensional image data so obtained are stored and processed by transducing the data into electric signals. Further, the component of the light from the object only can be effectively extracted from the optical image without impairing the information.

The assay method of the present invention employs, for supporting the object, a support that allows to penetrate of a liquid into itself and to absorb light. On the other hand, the marker enzyme can readily be brought into contact with the solution containing a chemiluminescent material, effectively reducing the background noises. This assay method is, therefore, simple and highly sensitive.

The present invention is not limited to the above preferred embodiment. Namely, it can be modified for various purposes. For example, the image treatment may include that the gravity center is extracted from a single photon image and then one picture element consisting of the gravity center is stored in a processor.

From the invention thus described, it will be obvious that the invention may be modified in many ways. Such variations are regarded as a departure from the spirit and scope of the invention, and all such modifications as would be obvious to one skilled in the art are intended to be included within the scope of the following claims.

The basic Japanese Application No. 280377/1994 filed on Nov. 15, 1994 is hereby incorporated by reference.

What is claimed is:

1. A method for assaying of an immunological complex by detecting chemiluminescence induced by reacting a catalyst label bound in the immunological complex with a chemiluminescent material, comprising:
   (a) contacting a sample suspected of containing a target antigen with an antibody attached to solid particles having a diameter of not more than 100 μm under conditions sufficient to bind the target antigen to said antibody;
   (b) adding a chemiluminescent detectant separately or with said antibody to form said immunological complex comprising the detectant and the target antigen bound to said antibody wherein the detectant comprises said catalyst label conjugated to at least one of said target antigen or said catalyst label, wherein said catalyst label is selected to induce chemiluminescence by reacting with said chemiluminescent material;

(c) separating free detectant from said immunological complex;

(d) distributing said solid particles substantially uniformly onto a surface of a support, said support being permeable to liquid and capable of absorbing light;

(e) contacting said solid particles distributed on said support surface with a solution of said chemiluminescent material to induce said chemiluminescence;

(f) acquiring an intensity profile of light from said support surface having said solid particles thereon, by imaging said support surface with an image pick-up device, said intensity profile consisting of a series of light intensity data of said support surface, each of said light intensity data of said support surface being acquired at each picture element;

(g) correcting said intensity profile with a processing device for diminishing noise, by subtracting a background intensity profile from said intensity profile by picture element, to obtain a corrected intensity profile consisting of a series of corrected light intensity data, said background intensity profile consisting of s series of light intensity data of a particle-less support surface acquired at each picture element by imaging said particle-less support surface using said image pick-up device; and (h) determining said target analyte in said sample by determining said immunological complex on each particle by extracting light intensity data which are not less than a detection limit, from said corrected intensity profile.

2. The method of claim 1, wherein said catalyst is an enzyme.

3. The method of claim 2, wherein said chemiluminescent material is a substrate for the enzyme.

4. The method of claim 3, wherein said chemiluminescent material is selected from the group consisting of indole derivatives and acridine derivatives.

5. The method of claim 1, wherein said catalyst is a porphyrin.

6. The method of claim 1, wherein the image pick-up device comprises:

(a) a first optical density means for (i) intensifying luminescence of incident light intensity of an optical image and (ii) outputting the intensified optical image, and (b) a second optical means for receiving the intensified optical image and converting the intensified optical image into an electrical signal.

7. The method of claim 1, wherein the support is selected from the group consisting of colored nitrocellulose membrane filter, colored nylon membrane filter, and colored polyvinylidene difluoride membrane filter.

* * * * *